United States Patent [19]

Gapinski

[11] Patent Number: 4,992,576

[45] Date of Patent: Feb. 12, 1991

[54] INTERMEDIATES FOR LEUKOTRIENE ANTAGONISTS

[75] Inventor: D. Mark Gapinski, Indianapolis, Ind.

[73] Assignee: Eli Lilly and Company, Indianapolis, Ind.

[21] Appl. No.: 501,339

[22] Filed: Mar. 27, 1990

Related U.S. Application Data

[63] Continuation of Ser. No. 200,350, May 31, 1988, abandoned, which is a continuation-in-part of Ser. No. 2,479, Jan. 12, 1987, abandoned.

[51] Int. Cl.$^5$ .................... C07C 12/75; C07C 49/784
[52] U.S. Cl. ........................ 560/52; 558/388; 558/389; 558/396; 558/405; 558/414; 562/426; 562/429; 562/441; 562/430; 562/451; 562/460; 562/450; 562/435; 548/252; 548/253
[58] Field of Search ............. 560/52; 558/388, 389, 558/396, 405; 562/426, 429, 441, 430, 451, 460, 450, 435; 548/252, 253

[56] References Cited

U.S. PATENT DOCUMENTS

| | | | |
|---|---|---|---|
| 3,600,437 | 8/1971 | Marshall | 562/465 |
| 3,657,430 | 4/1972 | Shen et al. | 424/230 |
| 4,035,376 | 7/1977 | Janssen et al. | 260/295 R |
| 4,166,819 | 9/1979 | Jones et al. | 548/253 |
| 4,242,121 | 12/1980 | Hawkins et al. | 71/93 |
| 4,337,353 | 6/1982 | Allais et al. | 562/460 |
| 4,567,184 | 1/1986 | Musser et al. | 514/277 |
| 4,695,648 | 9/1987 | Agback et al. | 560/53 |

FOREIGN PATENT DOCUMENTS

| | | |
|---|---|---|
| 0028063 | 5/1981 | European Pat. Off. . |
| 108592 | 5/1984 | European Pat. Off. . |
| 132366 | 1/1985 | European Pat. Off. . |
| 132367 | 1/1985 | European Pat. Off. . |
| 150166 | 7/1985 | European Pat. Off. . |
| 40-17135 | 8/1965 | Japan . |
| 42-18806 | 9/1967 | Japan . |
| 1293626 | 10/1972 | United Kingdom . |
| 1543964 | 4/1979 | United Kingdom . |

OTHER PUBLICATIONS

Gapinski et al, Fed. Proc., 2 (5), A1110 (1988).
Derwent 63208 D135, Abstracting Japanese Patent J5 6086-130.

Primary Examiner—David B. Springer
Attorney, Agent, or Firm—Robert A. Conrad; Leroy Whitaker

[57] ABSTRACT

This invention provides benzene derivatives which are leukotriene antagonists, formulations of those derivatives, intermediates for preparing the derivatives, and a method of using those derivatives for the treatment of conditions characterized by an excessive release of leukotrienes.

4 Claims, No Drawings

INTERMEDIATES FOR LEUKOTRIENE ANTAGONISTS

This application is a continuation of application Ser. No. 07/200,350, filed May 31, 1988, now abandoned, which is a continuation in part of application Ser. No. 07/002,479, filed Jan. 12, 1987, now abandoned.

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

Leukotriene B$_4$ (LTB$_4$) is a proinflammatory lipid which has been implicated in the pathogenesis of psoriasis, arthritis, chronic lung diseases, inflammatory bowel diseases, and other inflammatory states characterized by the infiltration and aggregation of polymorphonuclear leukocytes. Thus aggregated, the polymorphonuclear leukocytes liberate tissue-degrading enzymes and reactive chemicals causing the inflammation. Antagonism of LTB$_4$ should therefore provide a novel therapeutic approach to treatment of these conditions.

Similarly, antagonists of leukotriene D$_4$ (LTD$_4$) have been indicated for treating conditions characterized by the excessive release of LTD$_4$, including immediate type hypersensitivity reactions such as asthma and shock.

It is the object of this invention to provide novel chemical agents which are selective leukotriene antagonists that can be used therapeutically in the treatment of inflammation and allergic disorders such as asthma, where leukotrienes are thought to be causal mediators.

SUMMARY OF THE INVENTION

This invention provides compounds of the Formula I

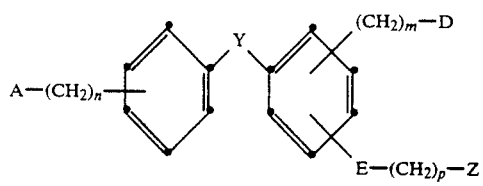

or a pharmaceutically acceptable base addition salt thereof, wherein A and D are each independently —COOR$_1$, —CN, or 5-tetrazolyl;

n is 0 or 1;

Y is —O—, —CO—, —S(O)$_t$—, —CONH—, —CH$_2$CO—, —C(=NOH)—, —CHOH—, —CH$_2$—, or —C(=CH$_2$)—;

m is 0–3;

E is —O— or —CH$_2$—;

p is 0–16; and

Z is —H or —G—Q where each R$_1$ is independently hydrogen or C$_1$–C$_3$ alkyl, G is a bond, —O—, —S-(O)$_t$—, —NH—, —CH=CH—, or —C≡C—, Q is phenyl or phenyl substituted with one or two substituents selected from the group consisting of halo, C$_1$–C$_3$ alkyl, C$_1$–C$_3$ alkoxy, acetyl, nitro, amino, trifluoromethyl, hydroxy, and —S(O)$_t$—(C$_1$–C$_3$ alkyl), and each t is independently 0–2.

Compounds wherein A and/or D are —CN or —COO(C$_1$–C$_3$ alkyl) are intermediates for preparing the corresponding tetrazoles and carboxylic acids.

Further provided by this invention is a method for treating immediate hypersensitivity conditions such as inflammation or asthma comprising the administration of an effective amount of a tetrazole or carboxylic acid derivative of the above formula.

This invention also provides a pharmaceutical formulation which comprises as an active ingredient a tetrazole or carboxylic acid compound of this invention as defined above associated with a pharmaceutically acceptable carrier therefor.

DETAILED DESCRIPTION AND PREFERRED EMBODIMENT

The present invention relates to new organic compounds that are useful in the treatment of immediate hypersensitivity reactions or as intermediates for preparing such compounds. A preferred group of compounds are the compounds of Formula Ia:

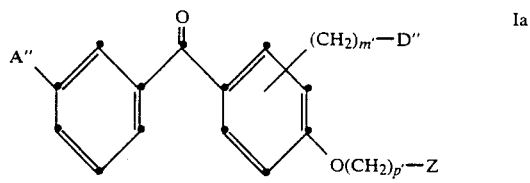

and pharmaceutically acceptable base addition salts thereof wherein

A'' and D'' are independently —COOH or 5-tetrazolyl, m' is 0–3, preferably 1 or 2, and p' is 4–12.

The following definitions refer to the various terms used throughout this disclosure.

The term "C$_1$–C$_3$ alkyl" refers to the straight and branched aliphatic radicals of 1 to 3 carbon atoms such as methyl, ethyl, propyl, and isopropyl. The term "C$_1$–C$_3$ alkoxy" refers to methoxy, ethoxy, propoxy, and isopropoxy. The term "halo" refers to fluoro, chloro, bromo, and iodo.

When A or D are carboxylic acid or 5-tetrazolyl moieties, the compounds of this invention include the pharmaceutically acceptable base addition salts thereof. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

It is recognized that when Y is —C(=NOH)— or —CHOH—, or when G is —CH=CH—, various stereoisomeric products may exist. This invention is not limited to any particular stereoisomer but includes all possible individual isomers and mixtures thereof.

The compounds of this invention may be prepared according to standard methods known in the art. For example, many of the ketone-containing derivatives of formula I may be prepared according to Scheme I:

whereas the latter reaction is usually complete in one hour at 20-30° C.

Similarly, transformation of the nitriles of formula IV to the corresponding tetrazoles can be accomplished by Scheme I

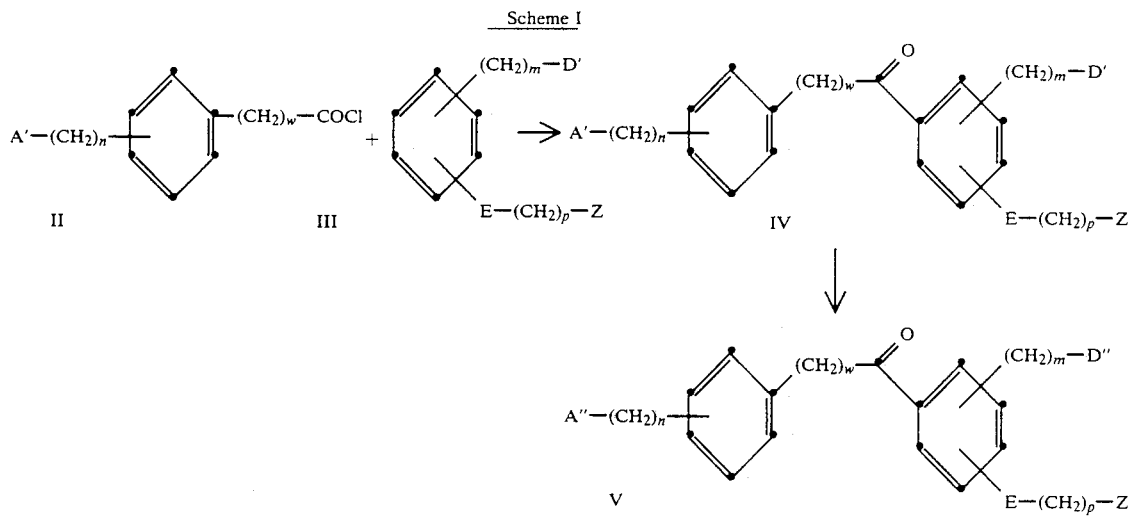

wherein:

A' and D' are independently —COO($C_1$-$C_3$ alkyl) or —CN, A" and D" are independently —COOH or 5-tetrazolyl, and w is 0 or 1. According to this scheme, an acid chloride of formula II is reacted with benzene derivative III under Friedel-Crafts acylation conditions to provide the corresponding ketone derivative IV. Any of a number of conditions to effect this transformation are known in the art and are operable. A preferred set of conditions comprises the reaction of II and III with a Lewis acid such as aluminum chloride in the presence of a non-reactive solvent, preferably dichloromethane. The reaction is best carried out at temperatures from about 0 to about 25° C. and is generally complete within 2-4 hours.

This reaction provides the ester and nitrile derivatives of formula IV which can then be transformed to the corresponding acid and/or tetrazole compounds of formula V according to standard methods. For example, hydrolysis of the esters of formula IV may be accomplished by any of a variety of acidic or basic conditions, preferably under aqueous conditions. Two preferred methods involve the use of lithium hydroxide in a solvent mixture of acetone/water or potassium hydroxide in a mixture of methanol/water. Under the former conditions, hydrolysis is generally complete in about 12-18 hours at temperatures from about 20-30° C.

any of a variety of standard methods. Generally, the nitrile is reacted with an azide reagent in a non-reactive solvent. Preferred conditions include the use of ammonium azide in dimethylformamide or tri-n-butylstannylazide in a non-reactive solvent such as dimethoxyethane or tetrahydrofuran. Under the latter conditions, the reaction is generally heated at or near the reflux temperature of the reaction mixture. The transformation is generally complete under these conditions in 2-3 days.

It is generally preferred, in compounds containing both a nitrile and an ester functionality, that the nitrile group be transformed into a tetrazole before hydrolysis of the ester.

A similar acylation procedure to prepare other ketone derivatives is described in Scheme II:

Scheme II

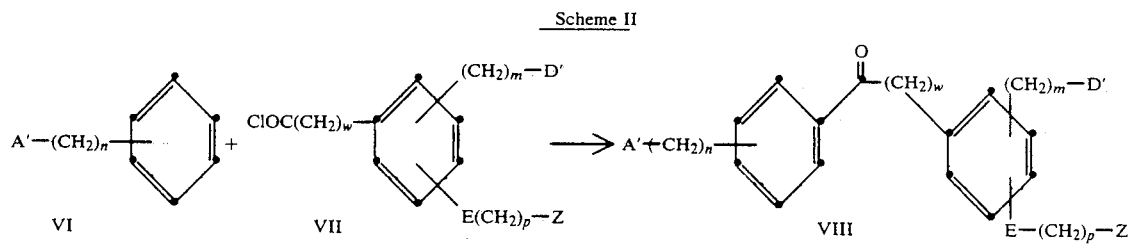

According to Scheme II, acid chloride VII is employed to acylate benzene derivative VI under the same Friedel-Crafts conditions as described above. This process yields intermediates of formula VIII which can then be transformed to the corresponding acids and tetrazoles by the same methods as described above.

In the special situation where the —($CH_2$)$_n$—COOH group is attached to a carbon atom adjacent to the point of attachment to the carbonyl moiety bridging the two phenyl rings, the modified procedure of Scheme III may be employed.

Scheme III

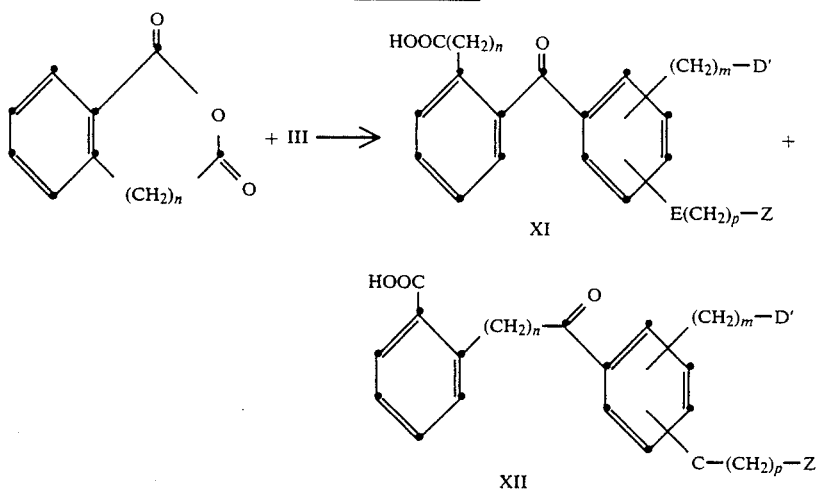

In this sequence, the cyclic anhydride IX is allowed to react with benzene derivative III to provide both the benzophenone acetic acid of formula XI as well as the phenylethanone derivative of formula XII. These compounds may be separated by standard methods, such as chromatography, and separately transformed into corresponding acids, tetrazoles, esters, etc. by standard techniques. The reaction of IX with III constitutes a modified Friedel-Crafts acylation as disclosed in Schemes I and II above. However, the preferred reaction conditions are generally the same.

The preparation of the diphenyl ether compounds of this invention (formula I, Y is —O—) and diphenyl sulfide analogs (Y is -S-) may be accomplished by any of a number of methods known in the art depending upon the particular substituents and their placement. The most general procedure is that of an Ullmann-type reaction as summarized in Scheme IV:

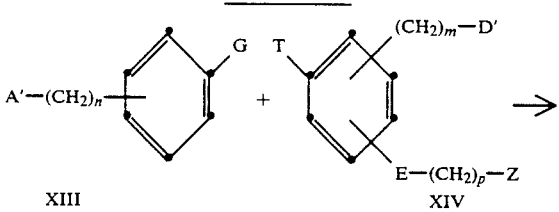

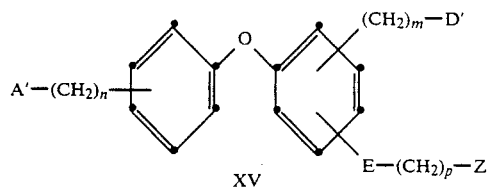

wherein one of G and T is iodo or bromo and the other of G and T is —OH or —SH. Under these reaction conditions, the phenol (or thiophenol) of formula XIII or XIV is treated with an alkali metal base of sufficient basicity so as to yield the metal (thio) phenolate. This formation is usually performed in situ, and the resulting nucleophile is then treated with the aryl halide of the other of formula XIII or XIV. Coupling to the diaryl ether of formula XV is promoted by the use of copper salts. Many variations on the Ullmann reaction are known in the art and can be employed in effecting the synthesis of compound XV. The compounds of formula XV may be transformed into the corresponding acids and tetrazoles in the same manner as previously described.

Other, more complicated, routes for preparing the diaryl ethers or sulfides may be employed. The particular sequence employed will depend upon the particular substituents desired and the relative position in the molecule.

One procedure for preparing some of the more preferred compounds of this invention is summarized in Scheme V:

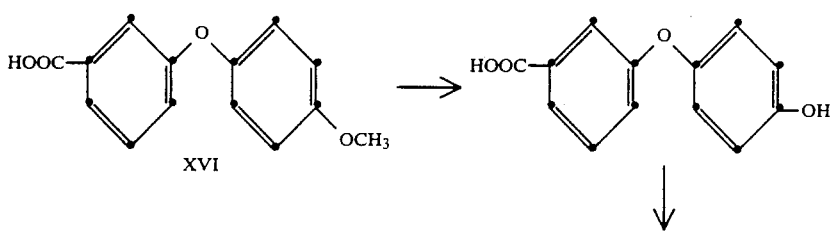

-continued
Scheme V

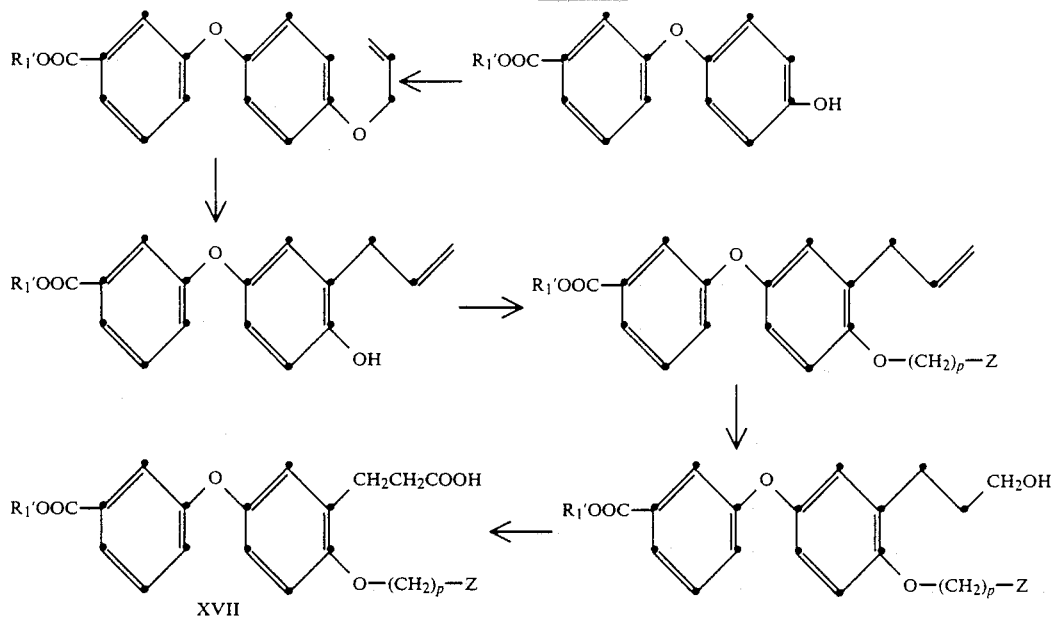

wherein $R_1'$ is $C_1$–$C_3$ alkyl. Scheme V depicts a general method of preparing compounds where there is a propionic acid substituent on a carbon atom adjacent to the —O—$(CH_2)_pZ$ functionality. Scheme V is therefore representative of the preparation of similar compounds having other functional groups as depicted in Formula I.

According to Scheme V, an anisole derivative such as that represented by formula XVI is dealkylated by standard means to the corresponding phenol (see description below). The carboxylic acid moiety is protected, usually by converting it to an ester derivative. The phenol is alkylated with an allyl halide to provide the corresponding allyl ether. Thermally rearranging the allyl ether (i.e., a Claisen rearrangement) provides a phenol wherein the allyl functionality is on the adjacent carbon atom. The phenol is then alkylated with the appropriate alkyl halide Z—$(CH_2)_p$—X, wherein X is a good leaving group such as iodo, bromo, chloro or mesyl, in the presence of a strong base, such as sodium hydride, and preferably in a non-reactive solvent, such as dimethylformamide. The resulting ether is then oxidized first to the corresponding propanol and then to the propionic acid derivative of formula XVII. Interconversions of the acids and esters may be performed by standard methods. Variations of the Scheme will be apparent to those skilled in the art and can, for example, be used to prepare the corresponding acetic acid derivatives, for example, by the oxidative cleavage of the allyl double bond.

Employing some of the same chemical aspects found in Scheme V, additional intraconversions are presented by Scheme VI:

Scheme VI

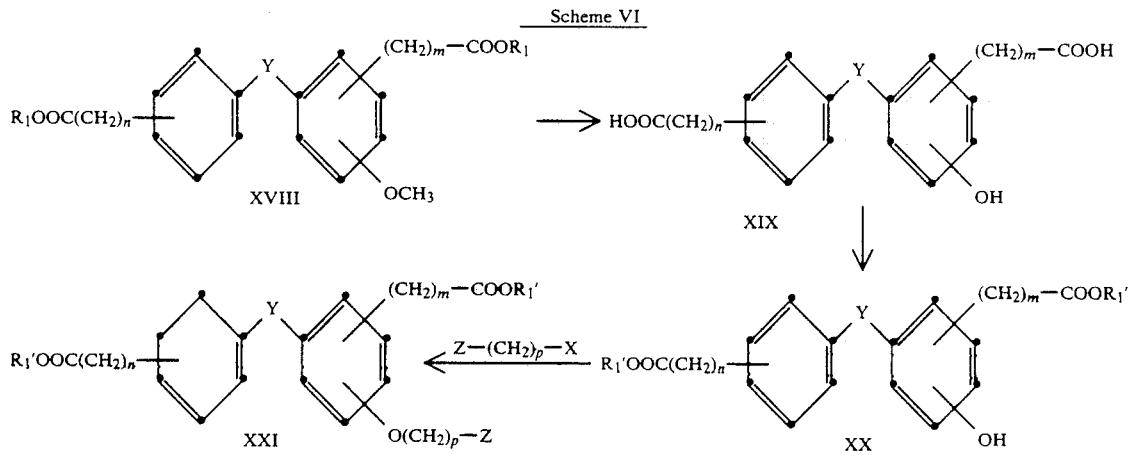

According to this transformation, the compound of formula XVIII, prepared by any of the other schemes and description which follows is prepared (i.e., Formula I wherein the —O—$(CH_2)_p$—Z functionality is methoxy). The methoxy group is removed by any of a number of methods known in the art to yield the corresponding phenol. One standard method for this transformation is the use of hydrobromic acid in acetic acid or treatment with molten pyridine hydrochloride. These methods usually also transform the carboxylic acid ester to the free carboxylic acid. The carboxylic acids are transformed into the diester compound XX which is treated with base and the appropriate alkylating agent Z—(CH$_2$)$_p$—X as employed in Scheme V. This alkylation provides the ether of formula XXI which may then be transformed to other derivatives according to other methods as described in this application.

Another alternate route for preparing the preferred propionic acids of this invention ((—CH$_2$)$_m$—D=—CH$_2$CH$_2$COOH), involves the direct introduction of this functionality from a phenol. Employing compound XXII as an illustrative starting material, the reaction is summarized in Scheme VII:

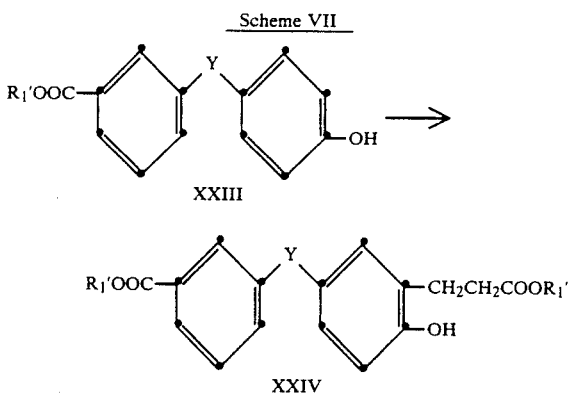

Following the procedure of Rapaport and Panetta, *J. Org. Chem.*, 47, 946 (1982), phenol XXIII is heated at reflux with a trialkyl orthoacrylate, such as triethyl orthoacrylate, and pivalic acid in an inert solvent such as toluene. After 6-18 hours of heating, the resulting cyclic orthoester intermediate is hydrolyzed, such as by stirring with ethanolic hydrochloric acid, to provide the desired intermediate XXIV. This phenolic intermediate can then be alkylated, hydrolyzed, and otherwise transformed as described earlier to provide the corresponding compound of this invention.

From the above methods of preparing the benzophenone compounds of this invention (formula I, Y is —CO—), compounds having various other Y functionalities may be prepared. For example, the benzophenone can be reduced to the corresponding carbinol (I, Y is —CHOH—). The most convenient method for effecting this transformation is treating the benzophenone with sodium borohydride in a solvent such as ethanol. To reduce the carbinol completely to the diphenylmethane derivative (I, Y is —CH$_2$—), reduction of the carbinol with hydrogen gas over a catalyst, such as palladium on carbon, is preferred. Standard reaction conditions in non-reactive solvents may be employed; acetic acid is a preferred solvent for this transformation. For either of these reduction steps, it is preferred that the ester intermediate be employed as compared with the carboxylic acid. After reduction, hydrolysis of the ester to the acid may be effected in the normal way.

Similarly, the benzophenone may be transformed into the oxime (Formula I, Y is —C(=NOH)—) upon treatment with hydroxylamine. The hydrochloride of hydroxylamine is usually employed although a non-reactive acidscavenging solvent, such as pyridine, is best employed. Once again, it is preferred that this transformation be performed on the ester form of the compound with hydrolysis to the carboxylic acid by standard methods to follow.

The ethylene analogs of this invention (I, Y is —C(=CH$_2$)—) may also be prepared from the benzophenones according to known methods. This transformation involves a Wittig reaction which is performed on a benzophenone compound before the introduction of any other reactive group, such a tetrazole moiety or carboxylic acid. Typically, a slight molar excess of an ylid precursor, such as methyl triphenylphosphine bromide, and a strong organic base, such as N-butyllithium, in a non-reactive solvent such as tetrahydrofuran, are employed. After the introduction of the ethene functionality, other derivatizations as previously described may be performed.

The carboxamide compounds of this invention (Y=—CONH—) are prepared by reacting an activated benzoic acid, e.g., a benzoyl chloride or similar intermediate, with an appropriately substituted aniline to provide intermediates of the Formula XXV:

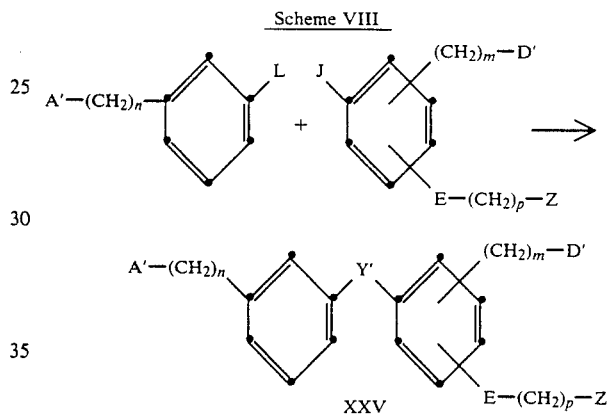

where one of J and L is —NH$_2$ and the other of J and L is —COCl or a related activated acid moiety, and Y' is —CONH—.

According to Scheme VIII, the aniline and activated benzoic acid are allowed to react usually in approximately equimolar amounts, preferably in the presence of a non-reactive solvent and an acid scavenger. This acylation procedure is well known to those skilled in the art and provides intermediates XXV which may be transformed into the compounds of this invention by methods as previously described. Alternatively, a hydroxy-aniline or -benzoic acid derivative can be employed to provide carboxamide intermediates analogous to intermediates XX, XXII, or XXIII which can be alkylated and otherwise transformed into the final compounds of the present invention by techniques as provided above.

The thio derivatives and intermediates of this invention (t is 0) may be transformed into the corresponding sulfoxide (t is 1) compounds upon treatment with a mild oxidizing agent, such as hydrogen peroxide in methanol, meta-chloroperoxybenzoic acid (MCPBA) in methylene chloride at 0° C., or an alkali metal periodate in aqueous alcohol. The corresponding sulfones (t is 2) are prepared from the thio or sulfoxide compounds on treatment with a strong oxidizing agent such as hydrogen peroxide in acetic acid or m-chloroperbenzoic acid in methylene chloride at 20-30° C. In addition, various compounds of Formula I can be prepared from other compounds, precursors, or intermediates of Formula I by standard methods such as hydrolysis, esterification, alkylation, oxidation, reduction, and the like, as are well known to those skilled in the art.

Intermediate compounds II, III, VI, VII, IX, XIII, XIV, and XVI, and any other necessary reagents are either commercially available, known in the literature, or can be prepared according to methods known in the art.

The following examples further illustrate the preparation of the intermediates and compounds of this invention. The examples are illustrative only and are not intended to limit the scope of the invention. Where structures were confirmed by infra-red, proton nuclear magnetic resonance, or mass spectral analysis, the compound is so designated by "IR", "NMR", or "MS", respectively.

EXAMPLE 1

3-[3-(Cyanomethyl)-4-(decyloxy)benzoyl]benzoic acid, ethyl ester

To a solution of 1.45 g of isophthalic acid, monoethyl ester monochloride in 25 ml of methylene chloride cooled to 0° C. by means of an external ice bath were added to 2.73 g aluminum chloride. After stirring for an hour, 1.87 g of 2-decyloxybenzyl cyanide were added. The reaction was stirred at 0° C. for 4 hours and then poured into ice water containing hydrochloric acid. After stirring for 1 hour, the layers were separated. The organic layer was washed with a saturated sodium bicarbonate solution, dried over magnesium sulfate, and concentrated in vacuo. The residue was purified by chromatography over silica gel eluting with a 5–30% ethyl acetate in hexane gradient. The appropriate fractions were pooled and concentrated in vacuo to provide 1.1 g of the title product as a colorless oil.

Analysis for $C_{28}H_{35}NO_4$: Calc.: C, 74.80; H, 7.85; N, 3.12; Found: C, 75.84; H, 8.83; N, 3.82.

EXAMPLE 2

3-[4-(Decyloxy)-3-(1H-tetrazol-5-ylmethyl)benzoyl]-benzoic acid, ethyl ester

A mixture of 1.0 g of the product from Example 1 and 2.2 g of tri-n-butylstannylazide in 30 ml of tetrahydrofuran was heated at reflux for 10 days. The reaction was allowed to cool to ambient temperature. A mixture of hydrochloric acid and methanol was added, and after stirring for 30 minutes, the mixture was concentrated in vacuo. The residue was purified by chromatography over silica gel eluting with a 30–75% ethyl acetate in hexane gradient which additionally contained 0.05% acetic acid. The appropriate fractions were cooled and concentrated to provide 592 mg of product. Recrystallization from hexane/ethyl acetate provided 580 mg of the desired title product.

Analysis for $C_{28}H_{36}N_4O_4$: Calc.: C, 68.27; H, 7.37; N, 11.37; Found: C, 68.56; H, 7.50; N, 11.55.

EXAMPLE 3

3-[4-(Decyloxy)-3-(1-tetrazol-5-ylmethyl]benzoyl]benzoic acid

A mixture of 580 mg of the product from Example 2 and 280 mg of lithium hydroxide in 10 ml of acetone and 1 ml of water were stirred for 6 hours. The mixture was concentrated in vacuo and the resulting residue was partitioned between diethyl ether and water. The layers were separated and the aqueous layer was extracted with diethyl ether. The aqueous layer was acidified with 1N hydrochloric acid and extracted with ethyl acetate. The ethyl acetate extract was dried over magnesium sulfate and concentrated to dryness. The residue was crystallized from hexane/ethyl acetate to provide 47 mg of the title product, m.p. 147–150° C.

Analysis for $C_{26}H_{32}N_4O_4$: Calc.: C, 67.08; H, 7.14; N, 12.03; Found: C, 67.35; H, 7.04; N, 11.76.

EXAMPLE 4–14

The following compounds were prepared according to the procedure of Example 1 from the appropriate acid chloride and the corresponding benzene derivative.

4. 2-(Decyloxy)-5-[3-(ethoxycarbonyl)benzoyl]benzeneacetic acid, ethyl ester, 45% yield, oil.

Analysis for $C_{30}H_{40}O_6$: Calc.: C, 72.55; H, 8.12; Found: C, 72.77; H, 8.13.

5. 5-(Decyloxy)-2-[3-(ethoxycarbonyl)benzoyl]benzeneacetic acid, ethyl ester, 47% yield, oil. NMR.

6. 2-(Decyloxy)-5-[3-(ethoxycarbonyl)benzoyl]benzenepropanoic acid, ethyl ester, 83% yield, oil.

Analysis for $C_{31}H_{42}O_6$: Calc.: C, 72.91; H, 8.29; Found: C, 72.69; H, 8.15.

7. 2-(Decyloxy)-5-[3-(ethoxycarbonyl)benzoyl]benzenebutanoic acid, ethyl ester, 34% yield, oil. NMR.

8. 2-(Decyloxy)-5-(3-cyanobenzoyl)benzene acetic acid, ethyl ester, 59% yield, oil. NMR, IR, MS.

9. 2-(Decyloxy)-5-(3-cyanomethylbenzoyl)benzenepropionic acid, ethyl ester, 54% yield, oil. NMR.

10. 2-(Tetradecyloxy)-5-[3-(ethoxycarbonyl)benzoyl]benzeneacetic acid, ethyl ester, 81% yield, oil. NMR.

11. 2-(Dodecyloxy)-5-[3-(ethoxycarbonyl)benzoyl]-benzeneacetic acid, ethyl ester, 5% yield, oil. NMR 12. 5-(3-Cyanobenzoyl)-2-(decyloxy)benzeneacetonitrile, 61% yield, m.p. 83–85° C.

Analysis for $C_{26}H_{30}N_2O_2$: Calc.: C, 77.58; H, 7.51; N, 6.96; Found: C, 77.30; H, 7.57; N, 6.72.

13. 2-(Decyloxy)-5-[3-(ethoxycarbonyl)benzoyl]benzenepropionitrile, 92% yield, oil. NMR 14. 2-(Decyloxy)-5-(3-cyanobenzoyl)benzene propanoic acid, ethyl ester, 68% yield, oil. NMR, MS.

EXAMPLES 15–19

The following compounds were prepared from the corresponding nitrile derivatives according to the procedure of Example 2.

15. 2-(Decyloxy)-5-[3-(1H-tetrazol-5-yl)benzoyl]benzeneacetic acid, ethyl ester, 16% yield, oil. IR, NMR, MS.

16. 2-(Decyloxy)-5-[3-(1H-tetrazol-5-ylmethyl)benzoyl]benzenepropanoic acid, ethyl ester, 68% yield, oil. NMR.

17. [4-(Decyloxy)-3-(1H-tetrazol-5-ylmethyl)-phenyl][3-(1H-tetrazol-5-yl)phenyl]methanone, 54% yield, m.p. 189–191° C.

Analysis for $C_{26}H_{32}N_8O_2$: Calc.: C, 63.91; H, 6.60; N, 22.93; Found: C, 64.02; H, 6.52; N, 22.84.

18. {4-(Decyloxy)-3-[2-(1H-tetrazol-5-yl)ethyl]-phenyl}[3-(ethoxycarbonyl)phenyl]methanone, 58% yield, oil. NMR, IR, MS.

19. 2-(Decyloxy)-5-[3-(1H-tetrazol-5-yl)benzoyl]benzenepropanoic acid, ethyl ester, 31% yield, m.p. 80–81° C.

Analysis for $C_{29}H_{38}N_4O_4$: Calc.: C, 68.75; H, 7.56; N, 11.06; Found: C, 68.91; H, 7.82; N, 11.13.

EXAMPLES 20-29

The following compounds were prepared from the corresponding esters according to the procedure of Example 3 by substituting potassium hydroxide in aqueous methanol as the base and solvent.

20. 5-(2-Carboxybenzoyl)-2-(decyloxy)benzeneacetic acid, 93% yield, m.p. 192° C. with decomposition. Analysis for: $C_{26}H_{32}O_6$: Calc.: C, 70.86; H, 7.35; Found: C, 70.95; H, 7.30.

21. 2-(3-Carboxybenzoyl)-5-(decyloxy)benzeneacetic acid, 60% yield, m.p. 92-94° C.

Analysis for $C_{26}H_{32}O_6$: Calc.: C, 70.89; H, 7.32; Found: C, 70.61; H, 7.19.

22. 5-(3-Carboxybenzoyl)-2-(decyloxy)benzenepropanoic acid, 66% yield, m.p. 114-116° C.

Analysis for $C_{27}H_{34}O_6$: Calc.: C, 71.34; H, 7.54; Found: C, 71.56; H, 7.79.

23. 5-(3-Carboxybenzoyl)-2-(decyloxy)benzenebutanoic acid, 72% yield, m.p. 158°-159° C.

Analysis for $C_{28}H_{36}O_6$: Calc.: C, 71.77; H, 7.74; Found: C, 71.48; H, 7.48.

24. 2-(Decyloxy)-5-[3-(1H-tetrazol-5-yl)benzoyl]benzeneacetic acid, 45% yield, m.p.=138°-140° C.

Analysis for $C_{26}H_{32}N_4O_6$: Calc.: C, 67.22; H, 6.94; N, 12.06; Found: C, 67.32; H, 7.13; N, 11.91.

25. 2-(Decyloxy)-5-[3-(1H-tetrazol-5-ylmethyl)benzoyl]benzenepropanoic acid, 46% yield, m.p. 137°-139° C.

Analysis for $C_{28}H_{36}N_4O_4$: Calc.: C, 68.27; H, 7.37; N, 11.37; Found: C, 68.47; H, 7.40; N, 11.21.

26. 5-(3-Carboxybenzoyl)-2-(tetradecyloxy)benzeneacetic acid, 4% yield, m.p. 143°-147° C.

Analysis for $C_{30}H_{40}O_6$: Calc.: C, 72.55; H, 8.12; Found: C, 72.27; H, 7.90.

27. 5-(3-Carboxybenzoyl)-2-(dodecyloxy)benzeneacetic acid, 27% yield, m.p. 144°-147° C.

Analysis for $C_{28}H_{36}O_6$: Calc.: C, 71.77; H, 7.74; Found: C, 69.86; H, 7.52.

28. 3-{4-(Decyloxy)-3-[2-(1H-tetrazol-5-yl)ethyl]benzoyl}benzoic acid, 63% yield, m.p. 160°-162° C.

Analysis for $C_{27}H_{34}N_4O_6$: Calc.: C, 67.90; H, 6.97; N, 11.73; Found: C, 67.83; H, 7.20; N, 11.54.

29. 2-(Decyloxy)-5-[3-(1H-tetrazol-5-yl)benzoyl]benzenepropanoic acid, 95% yield, m.p. 139°-140° C.

Analysis for $C_{27}H_{34}N_4O_4$: Calc.: C, 67.90; H, 6.97; N, 11.73; Found: C, 67.65; H, 6.93; N, 11.72.

EXAMPLES 30 AND 31

5-[2-(Carboxymethyl)benzoyl]-2-(decyloxy)benzenepropanoic acid, ethyl ester and
5-[(2-carboxyphenyl)acetyl]-2-(decyloxy)benzenepropanoic acid, ethyl ester To a suspension of 3.98 g of aluminum chloride in 100 ml of methylene chloride were added 5.0 g of ethyl 2-decyloxybenzene propanoate. After stirring for 5 minutes, 2.4 g of homophthalic anhydride were added and the reaction was stirred an additional 18 hours. The mixture was poured into an ice/1N hydrochloric acid mixture. When all solids were dissolved, the mixture was extracted 3 times with ethyl acetate. The combined extracts were concentrated to dryness and the residue was purified by chromatography over silica gel eluting with a 20-35% ethyl acetate in hexane gradient yielding the following products:

30. 5-[2-(Carboxymethyl)benzoyl]-2-(decyloxy)benzenepropanoic acid, ethyl ester, 1.3 g, m.p. 110°-111° C.

Analysis for $C_{30}H_{40}O_6$: Calc.: C, 72.55; H, 8.12; Found: C, 72.10; H, 7.99.

31. 5-[(2-Carboxyphenyl)acetyl]-2-(decyloxy)benzenepropanoic acid, ethyl ester, 0.9 g, oil. NMR.

EXAMPLE 32

5-(2-Carboxybenzoyl)-2-(decyloxy)benzeneacetic acid, ethyl ester

Following the procedure of Examples 30 and 31, phthalic anhydride and ethyl 2-decyloxybenzene acetate were reacted to provide the title product in 8% yield. The product was an oil.

Analysis for $C_{28}H_{36}O_6$: Calc.: C, 71.77; H, 7.74; Found: C, 71.54; H, 7.84.

EXAMPLES 33-35

The following products were obtained by hydrolysis of the corresponding esters by using the procedure of Example 3 or that taught for Examples 20-29.

33. 5-[2-(Carboxymethyl)benzoyl]-2-(decyloxy)benzenepropanoic acid, 82% yield, m.p. 177°-178° C.

Analysis for $C_{28}H_{36}O_6$: Calc.: C, 71.77; H, 7.74; Found: C, 72.05; H, 7.52.

34. 5-[(2-Carboxyphenyl)acetyl]-2-(decyloxy)benzenepropanoic acid, 75% yield, m.p. 92°-95° C.

Analysis for $C_{28}H_{36}O_6$: Calc.: C, 71.77; H, 7.74; Found: C, 71.70; H, 8.00.

35. 5-(2-Carboxybenzoyl)-2-(decyloxy)benzeneacetic acid, 63% yield, m.p. 154°-155° C.

Analysis for $C_{26}H_{32}O_6$: Calc.: C, 70.89; H, 7.32; Found: C, 70.98; H, 7.06.

EXAMPLES 36-38

The following compounds were prepared from the corresponding acid chloride and the appropriate benzene derivative according to the procedure of Example 1.

36. 2-(Octyloxy)-5-[3-(ethoxycarbonyl)benzoyl]benzeneacetic acid, ethyl ester, 15% yield, oil. NMR.

37. 2-(Decyloxy)-5-[4-(methoxycarbonyl)benzoyl]benzeneacetic acid, ethyl ester, 46% yield, oil. NMR.

38. 2-(Hexyloxy)-5-[3-(ethoxycarbonyl)benzoyl]benzeneacetic acid, ethyl ester, 12% yield, oil. NMR.

EXAMPLE 39

2-(Octyloxy)-5-{[3-(ethoxycarbonyl)phenyl]hydroxymethyl}benzeneacetic acid, ethyl ester To a solution of 220 mg of 2-(octyloxy)-5-[3-(ethoxycarbonyl)benzoyl]benzeneacetic acid, ethyl ester, in 25 ml of ethanol were added 20 mg of sodium borohydride. After 3 hours of stirring, 5 ml of water and 2 ml of hydrochloric acid were added. After stirring for 15 minutes, additional water was added until the solution turned cloudy. The mixture was poured into ethyl acetate and water. The layers were separated, the organic layer was washed three times with water, and the combined water extracts were back extracted with ethyl acetate. The ethyl acetate extracts were combined, dried over magnesium sulfate, and concentrated to dryness providing 190 mg of the desired title product as a colorless oil. NMR.

EXAMPLES 40-43

The following compounds were prepared from the corresponding benzophenones according to the procedure of Example 39.

40. 2-(Decyloxy)-5-{[3-(ethoxycarbonyl)phenyl]hydroxymethyl}benzeneacetic acid, ethyl ester, 100% yield, oil.

Analysis for $C_{30}H_{42}O_6$: Calc.: C, 72.26; H, 8.49; Found: C, 72.49; H, 8.78.

41. 2-(Decyloxy)-5-{[3-(ethoxycarbonyl)phenyl]hydroxymethyl}benzenepropanoic acid, ethyl ester, 79% yield, oil. NMR.

42. 2-(Decyloxy)-5-{[4-(methoxycarbonyl)phenyl]hydroxymethyl}benzeneacetic acid, ethyl ester, 51% yield. NMR.

43. 2-(Hexyloxy)-5-{[3-(ethoxycarbonyl)phenyl]hydroxymethyl}benzeneacetic acid, ethyl ester, 68% yield, oil. NMR.

EXAMPLES 44–48

The following compounds were prepared from the corresponding esters by either the procedure of Example 3 or the alternate procedure described for Examples 20–29.

44. 5-[(3-Carboxyphenyl)hydroxymethyl]-2-(octyloxy)benzeneacetic acid, 32% yield, m.p. 136°–138° C.

Analysis for $C_{24}H_{30}O_6$: Calc.: C, 69.55; H, 7.30; Found: C, 69.33; H, 7.34.

45. 5-[(3-Carboxyphenyl)hydroxymethyl]-2-(decyloxy)benzeneacetic acid, 54% yield, m.p. 123.5°–125° C.

Analysis for $C_{26}H_{34}O_6$: Calc.: C, 70.56; H, 7.74; Found: C, 70.60; H, 7.74.

46. 5-[(3-Carboxyphenyl)hydroxymethyl]-2-(decyloxy)benzenepropanoic acid, 80% yield, m.p. 147°–149° C.

Analysis for $C_{27}H_{36}O_6$: Calc.: C, 71.03; H, 7.95; Found: C, 71.24; H, 7.94.

47. 5-[(4-Carboxyphenyl)hydroxymethyl]-2-(decyloxy)benzeneacetic acid, 58% yield, m.p. 140°–141° C.

Analysis for $C_{26}H_{34}O_6$: Calc.: C, 70.56; H, 7.74; Found: C, 71.48; H, 7.06.

48. 5-[(3-Carboxyphenyl)hydroxymethyl]-2-(hexyloxy)benzeneacetic acid, 37% yield, m.p. 132°–135° C.

Analysis for $C_{22}H_{26}O_6$: Calc.: C, 68.38; H, 6.78; Found: C, 68.26; H, 6.73.

EXAMPLE 49

5-[(3-Ethoxycarboxyphenyl)methyl]-2-(decyloxy)benzenepropanoic acid, ethyl ester A solution of 820 mg of 2-(decyloxy)-5-{[3-(ethoxycarbonyl)phenyl]hydroxymethyl}benzenepropanoic acid, ethyl ester, in 20 ml of acetic acid and 0.5 ml of sulfuric acid was subjected to catalytic hydrogenation in the presence of palladium on carbon for approximately 18 hours. The reaction mixture was filtered, ethyl acetate was added to the filtrate, and the organic mixture was washed with water. The organic layer was dried over magnesium sulfate and concentrated to dryness. The residue was purified by preparative TLC on silica eluting with 15% ethyl acetate/hexane providing 151 mg of the desired title product as a pale yellow oil. NMR.

EXAMPLE 50

5-[(3-Carboxyphenyl)methyl]-2-(decyloxy)benzenepropanoic acid

The title compound was prepared from the corresponding ethyl ester by the alternate hydrolysis taught for Examples 20–29 in 22% yield, m.p. 146°–148° C.

Analysis for $C_{27}H_{36}O_5$: Calc.: C, 73.61; H, 8.24; Found: C, 74.96; H, 9.03.

EXAMPLE 51

5-[(3-Ethoxycarbonylphenyl)(hydroxyimino)methyl]-2-(decyloxy)benzenepropanoic acid, ethyl ester A mixture of 1.1 g of 2-(decyloxy)-5-[3-(ethyloxycarbonyl)benzoyl]benzenepropanoic acid, ethyl ester and 220 mg of hydroxylamine hydrochloride in 25 ml of pyridine was heated at 70° C. for approximately 18 hours. The reaction was allowed to cool to ambient temperature, ethyl acetate was added, and the solution was washed several times with 1N hydrochloric acid and water. The organic layer was dried over sodium sulfate and concentrated in vacuo to provide 1.04 g of the desired title product as an oil. NMR.

EXAMPLE 52

5-[(3-Carboxyphenyl)(hydroxyimino)methyl]-2-(decyloxy)benzenepropanoic acid

The title compound was prepared from a corresponding diester of Example 51 upon hydrolysis according to the procedure of Example 3. The desired product was recovered in 81% yield and had a melting point of 163°–165° C.

Analysis for $C_{27}H_{35}NO_6$: Calc.: C, 69.06; H, 7.51; N, 2.98; Found: C, 68.94; H, 7.22; N, 2.74.

The title product was also prepared in 81% yield directly from 5-(3-carboxybenzoyl)-2-(decyloxy)benzenepropanoic acid upon treatment with hydroxylamine hydrochloride according to the procedure of Example 51.

EXAMPLE 53

5-[1-(3-Ethoxycarboxyphenyl)ethenyl]-2-(decyloxy)benzene propanoic acid, ethyl ester A suspension of 840 mg of methyl triphenylphosphine bromide in 20 ml of dried tetrahydrofuran was treated with 1.2 ml of a 1.6M solution of n-butyllithium in hexane. After stirring for approximately 3 hours at room temperature, a solution of 1.0 g of 5-(decyloxy)-2-[3-(ethoxycarbonyl)benzoyl]benzenepropanoic acid, ethyl ester in 10 ml of dry tetrahydrofuran was added. After stirring for approximately 18 hours, the reaction was filtered and concentrated in vacuo. The residue was purified over silica gel eluting with a 0–15% ethyl acetate in hexane gradient. The appropriate fractions were pooled and concentrated to provide 600 mg of the desired title product. The proton NMR spectrum was consistent with the structure of the desired product.

EXAMPLE 54

5-[1-(3-Carboxyphenyl)ethenyl]-2-(decyloxy)benzenepropanoic acid

The title product was prepared from the diester of Example 53 upon treatment with lithium hydroxide according to the procedure of Example 3. The overall yield was 14% and the final product had a melting point of 74°–78° C.

Analysis for $C_{28}H_{36}O_5$: Calc.: C, 74.31; H, 8.02; Found: C, 74.18; H, 7.73.

EXAMPLE 55

5-[3-(Ethoxycarbonyl)phenoxy]-2-(decyloxy)benzenepropanoic acid

A. Preparation of 3-(4-methoxyphenoxy)benzoic acid.

To a suspension of 10.6 g of silver oxide in 75 ml of water were added 7 g of sodium hydroxide. Ten grams of 3-(4-methoxyphenoxy)benzaldehyde were added in dropwise fashion and the reaction mixture was heated to 60°–70° C. for one hour. The mixture was filtered, the filtrate was acidified to pH 2 with hydrochloric acid, and the resulting precipitate was recovered by filtration. Crystallization from ethanol/water afforded 6.6 g of the desired subtitle intermediate, m.p. 141°–143° C.

Analysis for $C_{14}H_{12}O_4$: Calc.: C, 68.85; H, 4.95; Found: C, 68.75; H, 4.83.

B. Preparation of 3-(4-hydroxyphenoxy)benzoic acid.

A mixture of 73 g of 3-(4-methoxyphenoxy)benzoic acid, 300 ml of 48% hydrobromic acid, and 600 ml of acetic acid was heated at reflux for 48 hours. The reaction mixture was allowed to cool to ambient temperature, poured into cold water, and extracted with ethyl acetate. The organic extracts were dried and concentrated in vacuo. The residue was crystallized from ethyl/hexane providing 39.41 g of the desired subtitle intermediate, m.p. 172°–174° C.

Analysis for $C_{13}H_{10}O_4$: Calc.: C, 67.82; H, 4.38; Found: C, 67.99; H, 4.64.

C. Preparation of 3-(4-hydroxyphenoxy)benzoic acid, ethyl ester.

A solution of 4.9 g of 3-(4-hydroxyphenoxy)benzoic acid, 1 ml of sulfuric acid, and 50 ml of ethanol were heated at reflux for 18 hours. The mixture was cooled to 25° C. and concentrated in vacuo. The residue was dissolved in a diethyl ether, washed with water, dried over sodium sulfate and concentrated in vacuo providing 5.2 g of the desired subtitle intermediate. The proton NMR spectrum was consistent with the structure of the desired product.

D. Preparation of 3-(4-allyloxyphenoxy)benzoic acid, ethyl ester.

To a solution of 5.17 g of the product from Example 55C above in 100 ml of dimethylformamide were added 0.79 g of a 60% dispersion of sodium hydride in mineral oil. After stirring for one hour, 2.39 g of allyl bromide were added. The mixture was stirred overnight. Ethyl acetate was added, the mixture was washed several times with a saturated sodium chloride solution, dried over sodium sulfate, and concentrated to dryness providing 4.97 g of the desired subtitle product. The NMR spectrum was consistent with the structure of the desired product.

E. Preparation of 3-(3-allyl-4-hydroxyphenoxy)benzoic acid, ethyl ester.

A solution of 4.97 g of 3-(4-allyloxyphenoxy)benzoic acid, diethyl ester in 25 ml of N,N-diethylaniline was heated to 210° C. for about 2 hours. After cooling, ethyl acetate was added to the mixture, and the organic solution was washed several times with water. The organic layer was dried over sodium sulfate and concentrated in vacuo. The residue was purified by chromatography over silica gel eluting with a 10–30% ethyl acetate in hexane gradient. The appropriate fractions were combined and concentrated in vacuo to provide 3.13 g of the desired subtitle intermediate. The NMR spectrum was consistent with the structure of the desired product.

F. Preparation of 3-(3-allyl-4-decyloxyphenoxy)benzoic acid, ethyl ester.

To a solution of 3.13 g of the intermediate of Example 55E in 150 ml of dimethylformamide were added 0.44 g of a 60% dispersion of sodium hydride in mineral oil. After stirring for 1 hour, 2.9 g of decyl iodide were added. The reaction was heated at 65° C. for 18 hours. After cooling to ambient temperature, ethyl acetate was added and the organic layer was washed several times with a saturated sodium chloride solution, dried and concentrated in vacuo. The residue was purified over silica gel eluting with a 5–15% ethyl acetate in hexane gradient. The appropriate fractions were combined and evaporated providing 3.69 g of the desired subtitle intermediate. The NMR spectrum was consistent with the structure of the desired product.

G. Preparation of 3-[4-decyloxy-3-(3-hydroxypropyl)phenoxy]benzoic acid, ethyl ester.

A solution of 1.85 g of the intermediate from Example 55F was dissolved in dry tetrahydrofuran and cooled to 0° C. Under a nitrogen atmosphere, 8.4 ml of a 0.5M solution of 9-borabicyclo[3.3.1]nonane in tetrahydrofuran were added and the reaction was stirred for 18 hours while allowing the solution to come to room temperature. The mixture was again cooled to 0° C. and 10 ml of a 3N aqueous solution of sodium acetate were added followed by the addition of 6.3 ml of 30% hydrogen peroxide. After stirring for 6 hours, the layers were separated. The organic layer was dried over sodium sulfate and concentrated in vacuo. The residue was purified by chromatography over silica gel eluting with a 5–25% ethyl acetate in hexane gradient. Upon concentration of the appropriate fractions, 1.2 g of the desired subtitle intermediate were obtained.

H. Preparation of 5-(3-ethoxycarbonylphenoxy)-2-(decyloxy)benzenepropanoic acid.

Two hundred milligrams of the intermediate from Example 55G were dissolved in diethyl ether. The solution was cooled to 0° C. and approximately 3 ml of Jones reagent were added. The reaction was stirred for 18 hours allowing the temperature to rise to room temperature. Diethyl ether and water were added, the layers were separated, and the organic layer was washed with a sodium bisulfite solution. The organic layer was dried and concentrated in vacuo. The residue was purified by preparative thin layer chromatography eluting with 30% ethyl acetate and hexane providing 38 mg of the desired title product.

EXAMPLE 56

5-(3-Carboxyphenoxy)-2-(decyloxy)benzenepropanoic acid

A solution of 510 mg of 5-(3-ethoxycarbonylphenoxy)-2-(decyloxy)benzenepropanoic acid in 20 ml of ethanol was treated with an excess of potassium hydroxide in a small amount of water. After stirring for 18 hours, the solution was concentrated in vacuo. Diethyl ether and water added, the layers were separated, and the aqueous layer was acidified with 1N hydrochloric acid. The aqueous layer was extracted with diethyl ether, and this extract was dried over sodium sulfate and concentrated in vacuo. Two crystallizations from ethyl acetate/hexane provided 200 mg of the desired title product, m.p. 102°–104° C.

Analysis for $C_{26}H_{34}O_6$: Calc.: C, 70.56; H, 7.74; Found: C, 71.28; H, 7.32.

EXAMPLE 57

5-[3-(Ethoxycarbonyl)benzoyl]-2-methoxybenzenepropanoic acid, ethyl ester

Following the procedure of Example 1, 30.6 g of isophthalic acid monoethyl ester monochloride and 30 g of ethyl 2-methoxybenzene propanoate were treated with 57 g of aluminum chloride in dichloromethane to provide 53.6 g of the desired title product, as an oil.

Analysis for $C_{22}H_{24}O_6$: Calc.: C, 68.74; H, 6.29; Found: C, 68.61; H, 6.50.

EXAMPLE 58

5-(3-Carboxybenzoyl)-2-hydroxybenzenepropanoic acid

A mixture of 41.5 g of 5-[3-(ethoxycarbonyl)benzoyl]-2-methoxybenzenepropanoic acid, ethyl ester and 410 g of pyridine hydrochloride were heated at 180° C. for 4 hours. After cooling, water was added to the mixture while hot. As the mixture cooled, the title product precipitated from solution. Filtration of the solids and crystallization from ethanol/water provided 31.1 g of the title product, m.p. 197°–200° C.

Analysis for $C_{17}H_{14}O_6$: Calc.: C, 64.97; H, 4.49; Found: C, 65.24; H, 4.73.

EXAMPLE 59

5-[3-(Ethoxycarbonyl)benzoyl]-2-hydroxybenzenepropanoic acid, ethyl ester

The product from Example 58 was heated for 4 days at reflux in ethanol in which one milliliter of sulfuric acid had been added. The mixture was cooled to ambient temperature and concentrated in vacuo. Ethyl acetate was added to the residue and the organic solution was washed with water, dried over sodium sulfate, and concentrated in vacuo. Purification by chromatography over silica gel eluting with ethyl acetate/hexane provided 21.52 g of the desired title product which crystallized on standing, m.p. 68°–70° C.

Analysis for $C_{21}H_{22}O_6$: Calc.: C, 68.10; H, 5.99; Found: C, 67.93; H, 5.91.

EXAMPLE 60

2-[6-(Phenylhexyl)oxy]-5-[3-(ethoxycarbonyl)benzoyl]benzenepropanoic acid, ethyl ester To a solution of 2.89 g of 5-[3-(ethoxycarbonyl)benzoyl]-2-hydroxybenzenepropanoic acid, ethyl ester in dimethylformamide were added 370 mg of a 50% dispersion of sodium hydride in mineral oil. After stirring for one hour at room temperature, two grams of the mesyl ester of 6-phenylhexanol were added. The reaction mixture was heated to 65° C. and stirred overnight. After cooling, the mixture was added to ethyl acetate, washed several times with a saturated sodium chloride solution, dried over sodium sulfate, and evaporated to dryness. Purification of the resulting solid over silica gel eluting with a 0–2% ethyl acetate in hexane gradient provided 1.88 g of the desired title product as an oil.

Analysis for $C_{33}H_{38}O_6$: Calc.: C, 74.74; H, 7.16; Found: C, 74.26; H, 7.27.

EXAMPLES 61–72

The following compounds were prepared from the appropriate phenol and corresponding mesylate according to the procedure of Example 60.

61. 2-[6-Phenylhex-5-enyl)oxy]-5-[3-(ethoxycarbonyl)benzoyl]benzenepropanoic acid, ethyl ester, 64% yield, oil.

Analysis for $C_{33}H_{36}O_6$: Calc.: C, 74.98; H, 6.86; Found: C, 75.22; H, 7.09.

62. 5-[3-(Ethoxycarbonyl)benzoyl]-2-[4-(phenylthio)butoxy]benzenepropanoic acid, ethyl ester, 42% yield, oil.

Analysis for $C_{31}H_{34}O_6S$: Calc.: C, 69.64; H, 6.41; Found: C, 68.39; H, 6.14.

63. 5-[3-(Ethoxycarbonyl)benzoyl]-2-[4-phenoxybutoxy]benzenepropanoic acid, ethyl ester, 59% yield, oil.

Analysis for $C_{31}H_{34}O_7$: Calc.: C, 71.80; H, 6.61; Found: C, 71.81; H, 6.41.

64. 5-[3-(Ethoxycarbonyl)benzoyl]-2-{[6-(4-methoxyphenyl)-5-hexenyl]oxy}benzenepropanoic acid, ethyl ester, 39.8% yield, oil.

Analysis for $C_{34}H_{38}O_7$: Calc.: C, 73.10; H, 6.86; Found: C, 70.47; H, 7.04.

65. 5-[3-(Ethoxycarbonyl)benzoyl]-2-{[6-(4-methoxyphenyl)hexyl]oxy}benzenepropanoic acid, ethyl ester, 66.5% yield, oil.

Analysis for $C_{34}H_{40}O_7$: Calc.: C, 72.83; H, 7.19; Found: C, 72.21; H, 7.72.

66. 2-{[6-(4-Chlorophenyl)hexyl]oxy}-5-[3-(ethoxycarbonyl)benzoyl]benzenepropanoic acid, ethyl ester, 46.7% yield, oil.

Analysis for $C_{33}H_{37}ClO_6$: Calc.: C, 70.14; H, 6.60; Found: C, 73.04; H, 7.26.

67. 5-[3-(Ethoxycarbonyl)benzoyl]-2-{(6-(4-fluorophenyl)hexyl]oxy}benzenepropanoic acid, ethyl ester, 56% yield, oil.

Analysis for $C_{33}H_{37}FO_6$: Calc.: C, 72.24; H, 6.80; Found: C, 72.50; H, 7.28.

68. 5-[3-(Ethoxycarbonyl)benzoyl]-2-{[6-(4-methylmercaptophenyl)-5-hexenyl]oxy}benzenepropanoic acid, ethyl ester, 70% yield, oil.

Analysis for $C_{34}H_{38}O_6S$: Calc.: C, 71.05; H, 6.66; Found: C, 71.19; H, 6.85.

69. 5-[3-(Ethoxycarbonyl)benzoyl]-2-{[6-(3-methoxyphenyl)-5-hexenyl]oxy}benzenepropanoic acid, ethyl ester, 41% yield, oil. IR, MS, NMR.

70. 5-[3-(Ethoxycarbonyl)benzoyl]-2-{[6-(2-methoxyphenyl)-5-hexenyl]oxy}benzenepropanoic acid, ethyl ester, 18% yield, oil. MS, IR, NMR.

71. 5-[3-(Ethoxycarbonyl)benzoyl]-2-{[6-(3-methoxyphenyl)hexyl]oxy}benzenepropanoic acid, ethyl ester, 94% yield, oil. MS, IR, NMR.

72. 5-[3-(Ethoxycarbonyl)benzoyl]-2-{[6-(2-methoxyphenyl)hexyl]oxy}benzenepropanoic acid, ethyl ester, 93% yield, oil. NMR.

EXAMPLE 73

5-[3-(Ethoxycarbonyl)benzoyl]-2-[4-(phenylsulfinyl)butoxy]benzenepropanoic acid, ethyl ester A solution of 317 mg of the compound of Example 62 in methylene chloride was cooled to −78° C. With stirring, 127 mg of meta-chloroperbenzoic acid were added to the reaction solution. After stirring 5 minutes, the external cooling bath was removed and stirring continued for ten additional minutes. Several drops of dimethylsulfide were added followed by ethyl acetate. The solution was washed with a sodium bicarbonate solution, dried over sodium sulfate, and concentrated in vacuo. The residue was purified by preparative thin layer chromatography providing 143 mg of the title product as an oil.

Analysis for $C_{31}H_{34}O_7S$: Calc.: C, 67.62; H, 6.22; Found: C, 67.39; H, 6.05.

EXAMPLE 74

5-[3-(Ethoxycarbonyl)benzoyl]-2-[4-(phenylsulfonyl)-butoxy]benzenepropanoic acid, ethyl ester Following the general procedure of Example 73, 326 mg of the sulfide from Example 62 were treated with 262 mg of MCPBA at room temperature for two hours providing 252 mg of the title product as an oil.

Analysis for $C_{31}H_{34}O_8S$: Calc.: C, 65.75; H, 6.00; Found: C, 64.71; H, 5.95.

EXAMPLES 75-87

The following compounds were prepared from the corresponding diesters according to the procedure of Examples 20-29.

75. 5-(3-Carboxybenzoyl)-2-[6-(phenylhexyl)oxy]-benzenepropanoic acid, 62% yield, m.p. 99°-101° C.

Analysis for $C_{29}H_{30}O_6$: Calc.: C, 73.40; H, 6.37; Found: C, 73.66; H, 6.41.

76. 5-(3-Carboxybenzoyl)-2-[6-(phenyl-5-hexenyl)oxy]benzenepropanoic acid, 70% yield, m.p. 125°-128° C.

Analysis for $C_{22}H_{28}O_6$: Calc.: C, 73.71; H, 5.97; Found: C, 73.92; H, 5.71.

77. 5-(3-Carboxybenzoyl)-2-[4-(phenylsulfinyl)butoxy]benzenepropanoic acid, 17% yield, m.p. 135°-137° C.

Analysis for $C_{27}H_{26}O_7S$: Calc.: C, 65.57; H, 5.30; Found: C, 66.60; H, 5.60.

78. 5-(3-Carboxybenzoyl)-2-[4-(phenylsulfonyl)-butoxy]benzenepropanoic acid, 92.5% yield, m.p. 197°-199° C.

Analysis for $C_{27}H_{26}O_8S$: Calc.: C, 63.52; H, 5.13; Found: C, 63.43; H, 4.93.

79. 5-(3-Carboxybenzoyl)-2-{[6-(4-methoxy-phenyl)-5-hexenyl]oxy}benzenepropanoic acid, 64% yield, m.p. 151°-152° C.

Analysis for $C_{30}H_{30}O_7$: Calc.: C, 71.70; H, 6.02; Found: C, 71.46; H, 6.11.

80. 5-(3-Carboxybenzoyl)-2-{[6-(4-methoxyphenyl)hexyl]oxy}benzenepropanoic acid, 53.9% yield, m.p. 100°-102° C.

Analysis for $C_{30}H_{32}O_7$: Calc.: C, 71.41; H, 6.39; Found: C, 71.57; H, 6.22.

81. 2-{[6-(4-Chlorophenyl)hexyl]oxy}-5-(3carboxybenzoyl)benzenepropanoic acid, 75% yield, m.p. = 119°-121° C.

Analysis for $C_{29}H_{29}ClO_6$: Calc.: C, 68.43; H, 5.74; Found: C, 68.55; H, 5.42.

82. 5-(3-Carboxybenzoyl)-2-{[6-(4-fluorophenyl)hexyl]oxy}benzenepropanoic acid, 51% yield, m.p. = 118°-120° C.

Analysis for $C_{29}H_{29}FO_6$: Calc.: C, 70.72; H, 5.93; Found: C, 70.97; H, 6.21.

83. 5-(3-Carboxybenzoyl)-2-{6-(4-methyl-mercaptophenyl)-5-hexenyl]oxy}benzenepropanoic acid, yield, m.p. = 138°-141° C.

Analysis for $C_{30}H_{30}O_6S$: Calc.: C, 69.48; H, 5.83; Found: C, 69.70; H, 5.92.

84. 5-(3-Carboxybenzoyl)-2-{[6-(3-methoxy-phenyl)-5-hexenyl]oxy}benzenepropanoic acid, 45% yield, m.p. = 122°-125° C.

Analysis for $C_{30}H_{30}O_7$: Calc.: C, 71.70; H, 6.02; Found: C, 71.94; H, 6.18.

85. 5-(3-Carboxybenzoyl)-2-{[6-(2-methoxy-phenyl)-5-hexenyl]oxy}benzenepropanoic acid, 33% yield, m.p. = 132-136° C.

Analysis for $C_{30}H_{30}O_7$: Calc.: C, 71.70; H, 6.02; Found: C, 71.98; H, 6.07.

86. 5-(3-Carboxybenzoyl)-2-{[6-(3-methoxyphenyl)hexyl]oxy}benzenepropanoic acid, 76% yield, m.p. = 88°-90° C.

Analysis for $C_{30}H_{32}O_7$: Calc.: C, 71.41; H, 6.39; Found: C, 71.62; H, 6.61.

87. 5-(3-Carboxybenzoyl)-2-{[6-(2-methoxyphenyl)hexyl]oxy}benzenepropanoic acid, 74% yield, m.p. = 125°-127° C.

Analysis for $C_{30}H_{32}O_7$: Calc.: C, 71.41; H, 6.39; Found: C, 71.67; H, 6.56.

EXAMPLES 88-89

The following compounds were prepared from the compound of Example 68 following the procedures of Examples 73 and 74, respectively.

88. 5-[3-(Ethoxycarbonyl)benzoyl]-2{[6-(4-methylsulfinylphenyl)-5-hexenyl]oxy}benzenepropanoic acid, ethyl ester, 73% yield, oil.

Analysis for $C_{34}H_{38}O_7S$: Calc.: C, 69.19; H, 6.43; Found: C, 69.00; H, 6.73.

89. 5-[3-(Ethoxycarbonyl)benzoyl]-2-{[6-(4-methylsulfonylphenyl)-5-hexenyl]oxy}benzenepropanoic acid, ethyl ester, 68% yield, oil.

Analysis for $C_{34}H_{38}O_8S$: Calc.: C, 67.31; H, 6.31; Found: C, 67.14; H, 6.54.

EXAMPLE 90-91

The following compounds were prepared from the corresponding diesters according to the procedure employed in Examples 20-29.

90. 5-(3-Carboxybenzoyl)-2-{[6-(4-methyl-sulfinylphenyl)-5-hexenyl]oxy}benzenepropanoic acid, yield, m.p. = 119°-122° C.

Analysis for $C_{30}H_{30}O_7S$: Calc.: C, 67.40; H, 5.66; Found: C, 67.96; H, 5.55.

91. 5-(3-Carboxybenzoyl)-2-{[6-(4-methyl-sulfonylphenyl)-5-hexenyl]oxy}benzenepropanoic acid, 70% yield, m.p. = 148°-150° C.

Analysis for $C_{30}H_{30}O_8S$:
Calc.: C, 65.44; H, 5.49;
Found: C, 65.68; H, 5.45.

EXAMPLE 92

5-{[3-(Ethoxycarbonyl)phenyl]thio}-2-{[6(4-methoxyphenyl)-5-hexenyl]oxy}benzenepropanoic acid ethyl ester A. Preparation of ethyl 5-(3-carboethoxyphenyl)thio-2-hydroxybenzenepropanate.

One gram of 4-(3-carboethoxyphenylthio)phenol, 1.6 g of triethylorthoacrylate, and 0.186 g of pivalic acid were heated at reflux overnight in 25 ml of toluene. After cooling, the mixture was diluted with diethyl ether, washed sequentially with 0.5N sodium hydroxide and a saturated sodium chloride solution, dried over magnesium sulfate, filtered and evaporated in vacuo to provide 1.53 g of the cyclic orthoester intermediate as a colorless oil. This material was dissolved in 40 ml of ethanol and 10 ml of 1N hydrochloric acid were added. The mixture was stirred at 25° C for 30 minutes. Two volumes of ethyl acetate were added and the mixture was washed twice with water. The organic layer was dried and evaporated in vacuo. The residue was purified by high pressure liquid chromatography over silica gel eluting with a 0–25% ethyl acetate in hexane gradient. The appropriate fractions were combined and concentrated in vacuo to provide 1.18 g of the subtitle intermediate as a colorless oil.

Analysis for $C_{20}H_{22}O_5S$:
Calc.: C, 64.15; H, 5.92; S, 8.56;
Found: C, 63.98; H, 6.00; S, 8.80.

B. Preparation of 5-{[3-(Ethoxycarbonyl)phenyl]thio}-2-{[6-(4-methoxyphenyl)-5-hexenyl]oxy}-benzenepropanoic acid ethyl ester.

The title product was prepared according to a modification of the procedure reported in Example 60. A solution of 6-(4-methoxyphenyl)-5-hexenyl alcohol in diethyl ether was cooled to 0° C. To the alcohol solution were added 0.71 ml of triethylamine followed by the introduction of 0.38 ml of methanesulfonyl chloride. The reaction was stirred, allowing the mixture to come to room temperature, approximately three hours. Water was added to the mixture and the layers separated. The ether layer was washed with water, dried and concentrated in vacuo. To this mesylate intermediate were added 100 ml of methyl ethyl ketone and approximately 100 mg of potassium iodide. After refluxing for 30 minutes, 1.84 g of the phenol intermediate from Example 92A above were added together with 0.68 g of potassium carbonate. The mixture was heated at reflux overnight. After cooling to room temperature, the mixture was filtered and the filtrate washed with a sodium bicarbonate solution. The organic solution was dried and concentrated in vacuo. The residue was purified by high pressure liquid chromatography over silica gel eluting with a 0–20% ethyl acetate in hexane gradient. The appropriate fractions were combined and concentrated in vacuo to provide 0.76 g of the desired title product. NMR.

EXAMPLE 93

5-[3-(Carboxyphenyl)thio]-2-{[6-(4-methoxy-phenyl)-5-hexenyl]oxy]benzenepropanoic acid The title product was prepared in 57% yield from the diester intermediate of Example 92 following the procedure of Example 56, m.p. 129°–130° C.

Analysis for $C_{29}H_{30}O_6S$:
Calc.: C, 68.75; H, 5.97;
Found: C, 68.99; H, 5.85.

EXAMPLE 94

5-{[3-(Ethoxycarbonyl)phenyl]sulfinyl]-2-{[6-(4-methoxyphenyl)-5-hexenyl]oxy}benzenepropanoic acid ethyl ester A. Preparation of ethyl 5-(3-carboethoxy-phenyl)sulfinyl-2-hydroxybenzenepropanoate.

To a solution of 2.11 g of the sulfide intermediate of Example 92A above in methylene chloride cooled to 0° C. were added 1.1 g of 85% meta-chloroperoxybenzoic acid. After stirring for one hour, the mixture was filtered, and the filtrate was dried and then concentrated in vacuo. The residue was purified by high pressure liquid chromatography over silica gel eluting with a 0–30% ethyl acetate in hexane gradient. The appropriate fractions were combined and concentrated in vacuo to provide 1.67 g of the desired subtitle intermediate as an oil.

Analysis for $C_{20}H_{22}O_6S$:
Calc.: C, 61.52; H, 5.68; S, 8.21;
Found: C, 61.27; H, 5.72; S, 8.18.

B. Preparation of 5-{[3-(ethoxycarbonyl)phenyl]sulfinyl}-2-{[6-(4-methoxyphenyl)-5-hexenyl]-}benzenepropanoic acid ethyl ester.

The title product was prepared in 54% yield from 1.26 g of the intermediate of Example 94A above according to the procedure used in Example 92B. The product was an oil.

Analysis for $C_{33}H_{38}O_7S$:
Calc.: C, 68.49; H, 6.62; S, 5.54;
Found: C, 68.23; H, 6.79; S, 5.40.

EXAMPLE 95

5-[(3-Carboxyphenyl)sulfonyl]-2-{[6-(4-methoxyphenyl)-5-hexenyl]oxy}benzenepropanoic acid The title product was prepared in 58% yield from the diethyl ester intermediate of Example 94 according to the procedure of Example 56, m.p. 145°–148° C.

Analysis for $C_{29}H_{30}O_7S$: Calc.: C, 66.65; H, 5.79; S, 6.14; Found: C, 66.71; H, 5.87; S, 6.27.

EXAMPLE 96

5-{[3-(Ethoxycarbonyl)phenyl]sulfonyl}-2-{[6-(4-methoxyphenyl)-5-hexenyl]oxy}benzenepropanoic acid ethyl ester A. Preparation of 5-{[3-(ethoxycarbonyl)phenyl]sulfonyl]-2-hydroxybenzenepropanoic acid ethyl ester.

The title product was prepared from 1.71 g of the sulfide of Example 92A and 1.89 g of 85% meta-chloroperoxybenzoic acid following the general procedure employed in Example 94A. The intermediate was an oil.

Analysis for $C_{20}H_{22}O_7S$: Calc.: C, 59.10; H, 5.46; S, 7.89; Found: C, 58.82; H, 5.41; S, 7.87.

Preparation of 5-{[3-(ethoxycarbonyl)phenyl]sulfonyl}-2-{[6-(4-methoxyphenyl)-5-hexenyl]-oxy}benzenepropanoic acid ethyl ester.

The title product was prepared in 65% yield as an oil from 1.27 g of the sulfone intermediate of Example 96A according to the procedure of Example 92B.

Analysis for $C_{33}H_{38}O_8S$: Calc.: C, 66.65; H, 6.44; S, 5.39; Found: C, 66.94; H, 6.54; S, 5.54.

EXAMPLE 97

5-[3-Carboxyphenyl])sulfonyl]-2-{[6-(4-methoxyphenyl)-5-hexenyl]oxy}benzenepropanoic acid The title product was prepared in 68% yield from the corresponding diester of Example 96 according to the procedure of Example 56, m.p. 134°–136° C.

Analysis for $C_{29}H_{30}O_8S$: Calc.: C, 64.67; H, 5.61; S, 5.95; Found: C, 64.95; H, 5.59; S, 6.03.

EXAMPLE 98

2-{[6-(4-Methoxyphenyl)-5-hexynyl]oxy}-5-[3-(ethoxycarbonyl)benzoyl]benzenepropanoic acid ethyl ester.

Following the procedure of Example 92B, 0.38 g of 6-(4-methoxyphenyl)-5-hexynyl alcohol were converted to the mesyl ester and reacted with 0.69 g of 5-[3(ethoxycarbonyl)benzoyl]-2-hydroxybenzenepropanoic acid ethyl ester to provide the title product in 55% yield as an oil.

Analysis for $C_{34}H_{36}O_7$: Calc.: C, 73.36; H, 6.52; Found: C, 73.11; H, 6.43.

EXAMPLE 99

2-{[6-(4-Methoxyphenyl)-5-hexynyl]oxy}-5-(3-carboxybenzoyl)benzenepropanoic acid The title product was prepared in 59% yield from the corresponding diester of Example 98 according to the procedure of Example 56, m.p. 144°–146° C.

Analysis for $C_{30}H_{28}O_7$: Calc.: C, 71.99; H, 5.64; Found: C, 71.90; H, 5.59.

EXAMPLE 100

2-{[6-(4-Acetylphenyl)hexyl]oxy}-5-[3(ethoxycarbonyl)benzoyl]benzenepropanoic acid ethyl ester In a manner analogous to Example 92B, 2.85 g of 6-(4-acetylphenyl)hexanol were converted into its mesylate and reacted with 1.78 g of 5-[3-(ethoxycarbonyl)-benzoyl]-2-hydroxybenzenepropanoic acid ethyl ester to provide 2.21 g of the desired title product as a pale yellow oil.

Analysis for $C_{35}H_{40}O_7$: Calc.: C, 73.40; H, 7.04; Found: C, 73.24; H, 7.17.

EXAMPLE 101

2-{[6-(4-Acetylphenyl)hexyl]oxy-}5-(3carboxybenzoyl]benzenepropanoic acid

The title product was prepared in 66% yield from the diester of Example 100 following the procedure of Example 56, m.p. 139°–141° C.

Analysis for $C_{31}H_{32}O_7$: Calc.: C, 72.08; H, 6.24; Found: C, 72.35; H, 6.47.

EXAMPLE 102

5-[(3-Carboxybenzoyl)amino]-2-[6-(phenylhexyl)oxy]-benzenepropanoic acid

A. Preparation of ethyl 2-hydroxy-5-nitrobenzenepropanoate and ethyl 2-hydroxy-3-nitrobenzene propanate.

A mixture of 8.8 g of ethyl 2-hydroxybenzenepropanoate in 40 ml of acetic acid was cooled to 0° C. A mixture of 2.05 ml of nitric acid and 10 ml of acetic acid was added in dropwise fashion. After the addition was complete, the reaction was allowed to stir for 30 minutes at 0° C. The mixture was poured onto ice and extracted with ethyl acetate. The organic extracts were washed with water, dried over magnesium sulfate, filtered, and concentrated in vacuo. The residue was purified by high pressure liquid chromatography over silica gel eluting with a 10–30% ethyl acetate in hexane gradient. Fractions combining the desired 5-nitro isomer were combined and concentrated in vacuo providing 3.08 g of the desired title product as a pale yellow solid, m.p. 87°–89° C. Later fractions provided 3.08 g of the 3-nitro isomer.

Ethyl 2-hydroxy-5-nitrobenzenepropanate

Analysis for $C_{11}H_{13}NO_5$: Calc.: C, 55.23; H, 5.48; N, 5.86; Found: C, 54.99; H, 5.62; N, 5.78.

Ethyl 2-hydroxy-3-nitrobenzenepropanoate, NMR, IR, MS

B. Preparation of ethyl 2-[6-(phenylhexyl)oxy]-5-nitrobenzene propanoate.

The subtitle intermediate was prepared from ethyl 2-hydroxy-5-nitrobenzenepropanoate and the methanesulfonate ester of 6-phenylhexanol in 25% yield according to the procedure of Example 92A. NMR C. Preparation of ethyl 2-[6-(phenylhexyl)-oxy]-5-aminobenzenepropanoate.

Six hundred milligrams of the nitro compound of Example 102B above were dissolved in ethyl acetate and placed in a fiberglass-coated hydrogenation flask. Approximately 50 mg of a 10% palladium on carbon catalyst were added and the mixture shaken gently under approximately 30 p.s.i. of a hydrogen atmosphere. Approximately one hour later, hydrogen uptake ceased and the reaction mixture was filtered through a Celite mat. The filtrate was evaporated and the crude amine obtained (520 mg) was used directly for the subsequent acylation step without further purification.

D. Preparation of 5-[(3-carboxybenzoyl)-amino]-2-[6-(phenylhexyl)oxy]benzenepropanoic acid.

Two lots of amino intermediate prepared according to Example 102C above (1.42 g) in 25 ml of pyridine were added 0.81 g of 3-carboethoxybenzoyl chloride. After stirring for two hours, ethyl acetate was added and the mixture washed sequentially with 1N sodium hydroxide, 1N hydrochloric acid, and a saturated sodium chloride solution. The organic layer was dried and concentrated in vacuo. The residue was purified over silica gel by high pressure liquid chromatography eluting with a 10–30% ethyl acetate in hexane gradient. The appropriate fractions were combined and concentrated in vacuo to give 860 mg of the diethyl ester of the title compound. This material was hydrolyzed according to the procedure of Example 56 to provide 440 mg of the desired title product, m.p. 199°–200° C.

Analysis for $C_{29}H_{31}NO_6$: Calc.: C, 71.15; H, 6.38; N, 2.86; Found: C, 71.34; H, 6.45; N, 2.77.

EXAMPLE 103

5-[3-(1H-Tetrazol-5-yl)benzoyl]-2-{[6-(4-methoxyphenyl)-5-hexenyl]oxy}benzenepropanoic acid Following the general procedure of Example 92B, 1.63 g of 6-(4-methoxyphenyl)-5-hexenyl alcohol were converted to its mesyl ester and reacted with 2.45 g of 5-(3-cyanobenzoyl)-2-hydroxybenzenepropanoic acid methyl ester to provide 1.34 g of 5-(3-cyanobenzoyl)-2{[6-(4-methoxyphenyl)-5-hexenyl]oxy]benzenepropanoic acid methyl ester, m.p. 65°–67° C.

This intermediate can then be converted into the title product by treatment with triethyl ammonium azide in dimethylformamide, following the procedure of Berstein et al., Synthesis, 1133 (1987), followed by hydrolysis according to the procedure of Example 56.

EXAMPLE 104

3-[(3-Carboxybenzoyl)amino]-2-[6-(phenylhexyl)oxy]-benzenepropanoic acid

The title product was prepared from ethyl 2-hydroxy-3-nitrobenzenepropanoate (Example 102A) following the procedures of Examples 102B, 102C, and 102D in 4% overall yield, m.p. 176°–178° C.

Analysis for $C_{29}H_{31}NO_6$: Calc.: C, 71.15; H, 6.38; N, 2.86; Found: C, 71.02; H, 6.15; N, 2.92.

EXAMPLE 105

5-[{Carboxyphenyl)amino]carbonyl}-2-[6-(phenylhexyl)oxy]benzenepropanoic acid

4-Hydroxybenzoic acid can be converted into the corresponding acid chloride upon treatment with thionyl chloride in pyridine. The reaction of equimolar amounts of 4-hydroxybenzoyl chloride and ethyl 3- aminobenzoate in pyridine yields N-(3-ethoxycarbonylphenyl)-4-hydroxybenzamide which can be transferred into ethyl 5-{[3-(ethoxycarbonylphenyl)amino]carbonyl}-2-hydroxybenzenepropanoate according to the procedure of Example 92A. Alkylation of this phenol according to the procedure of Example 60 followed by hydrolysis of the resulting diester by the method of Example 56 will provide the title compound.

The compounds of Formula I should be useful in treating any condition, including clinical conditions, which is characterized by the excessive release of leukotrienes $B_4$ or $D_4$ These conditions include immediate type hypersensitivity reactions such as asthma. Evidence obtained over the past few years has shown the presence of leukotrienes in sputum of patients with chronic bronchitis (Turnbull, et al., Lancet II, 526 (1977)) and cystic fibrosis (Cromwell, et al., Lancet II, 164 (1981)), suggesting a role of leukotrienes in the pathology of those diseases. Furthermore, Lewis and colleagues [Int. J. Immunopharmacology, 4, 85 (1982)]have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes. The compounds of Formula I also antagonize the biological effects of leukotriene $C_4$ ($LTC_4$) which appears to be distinct from and unrelated to the effect upon $LTB_4$ or $LTD_4$ receptors. The compounds are therefore useful in any disease state or condition where $LTC_4$ contributes to pathology, such as asthma, allergy, myocardial infarction, inflammatory bowel diseases and stroke.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or susceptible to a condition characterized by an excessive release of leukotrienes with a compound of formula I will be measured by the regression or prevention of the symptoms of the condition.

Leukotriene $D_4$ antagonism was demonstrated by the following test procedure:

Male, Hartley guinea pigs weighing 200-450 grams were killed by decapitation. A section of terminal ileum was removed, the lumen cleaned, and the tissue divided into 2.5 cm segments. The ilea were mounted in 10 ml tissue baths containing Krebs-bicarbonate solution of the following composition in mmoles/liter: KCl, 4.6; $CaCl_2.2H_2O$, 1.2; $KH_2PO_4$, 1.2; $MgSO_4.7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. Isometric measurements were made with a Grass FTO3C force-displacement transducer and recorded on a Grass polygraph as change in grams of force. A passive force of 0.5 g was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug.

A more detailed analysis of $LTD_4$ antagonism was then made. In these experiments, cumulative concentration-response curves were obtained to $LTD_4$ in guinea pig ileum and trachea. This was followed by a 30 minute incubation with various concentrations of the experimental drug. The concentration response curve to $LTD_4$ was then repeated in the presence of the antagonist. Only one concentration of antagonist was used on a single tissue. $K_B$ values were calculated by the method of Furchgott [Ann. N.Y. Acad. Sci., 139,553 (1967)]using the following equation.

$$K_B = \frac{[\text{Antagonist}]}{\text{Dose Ratio} - 1}$$

Dose ratio refers to the concentration of agonist required to elicit 50 percent of the maximal response ($ED_{50}$) in the presence of the antagonist divided by the $ED_{50}$ in the absence of the antagonist. Calculations were performed with the aid of a computer and a digital plotter. The $pA_2$ is then calculated as the negative log of $K_B$ when the slope of the Schild plot is not significantly different from unity.

The testing of the compounds of Formula I is summarized in Table I.

TABLE I

| Antagonism of $LTD_4$ by Compounds of Formula I | |
|---|---|
| Compound of Example No. | $pA_2$* |
| 3 | 6.3 |
| 7 | 6.8 |
| 20 | 6.0 |
| 21 | 5.85 |
| 22 | 5.71 |
| 24 | 6.4 |
| 25 | 6.2 |
| 28 | 6.49 |
| 29 | 6.02 |
| 33 | 5.94 |
| 34 | 5.72 |
| 45 | 5.7 |
| 48 | 5.1 |
| 52 | 6.18 |
| 56 | 6.32 |
| 66 | 6.24 |

*Estimated

The compounds of this invention are also receptor antagonists of leukotriene $B_4$. As such, they are capable of blocking the biological effects of this leukotriene such as neutrophil aggregation, chemotaxis, and degranulation, as demonstrated in the following test systems.

$LTB_4$ Induced Aggregation Assay

Neutrophils were elicited by intraperitoneally injecting 20 ml of Dulbecco's calcium and magnesium deficient phosphate buffered saline (PBS) containing 2% oyster glycogen into each of two male Hartley guinea pigs. Eighteen hours later, cells accumulating in the peritoneal cavity were harvested by washing the peritoneum with approximately 100 ml of PBS containing 10 units/ml of heparin. The cells were centrifuged at 200 g for 8 min. and the supernatant fluid discarded. Erythrocytes present in the pellet were lyzed by vigorous agitation of the cells in 9 ml of ice-cold distilled water for approximately 30 seconds. Physiological osmolarity was restored by adding 1.5 ml of 0.6 M KCl. Twelve milliliters of PBS were added and the resuspended cells centrifuged at 200 g for 8 min. at 4°. The pellet was resuspended in 5 ml PBS. The cell concentration was determined and additional buffer added to make the concentration $1\times 10^7$ cells per ml. This isolation procedure resulted in cell populations of $>90\%$ neutrophils and $>90\%$ viability.

The aggregation assay was carried out by measuring the amount of $LTB_4$ induced cell aggregation with a Payton single channel aggregometer, model 300B. The apparatus was calibrated by placing a cuvette containing the cell suspension in it and adjusting the zero knob so that the recorder pen rested at 1 mV. A cuvette containing 20% less cells was then inserted into the aggregometer and the output knob adjusted so that the recorder pen rested at 9 mV. With these settings an 8 mV change causes the recorder pen to move 200 mm. When conducting an assay, 0.5 ml of cell suspension ($5\times 10^6$ cells) was added to each cuvette. Five microliters of a solution of test compound were then added. Most compounds were initially dissolved in DMSO at $1\times 10^{-2}M$ and then diluted appropriately with PBS so that the test compound concentration was $1\times 10^{-5}$ to $1\times 10^{-7}M$ and the test DMSO concentration was 0.1% or less. A few of the more water insoluble compounds were first dissolved in DMSO at 1 to $6\times 10^{-3}M$ and then diluted appropriately with PBS. The test concentration of DMSO was never higher than 1%. After a 2 minute equilibration period of cells and test compound, 5 μl of a solution containing $CaCl_2$ (100 mM) and $MgCl_2$ (50 mM) were added. One minute later, 5 μl of PBS containing $LTB_4$ ($3\times 10^{-7}M$) were added. The change occurring in the amount of light transmitted during the subsequent minute was measured. In the absence of test compound, this amount of $LTB_4$ usually caused a change in the recorder pen position of 120–150 mm. During a typical experiment, several measurements of the amount of aggregation induced by $LTB_4$ were made and an average value determined. The effect of a test compound on this aggregation was determined by the following formula:

$$\text{Percent Inhibition} = \frac{\text{Aggregation with } LTB_4 - \text{Aggregation with } LTB_4 + \text{Compound}}{\text{Aggregation with } LTB_4} \times 100$$

The results of these experiments are summarized in Table II.

TABLE II

Inhibition of $LTB_4$ Induced Aggregation

| Example No. | Drug Concentration* | | |
|---|---|---|---|
| | $10^{-5}M$ | $10^{-6}M$ | $10^{-7}M$ |
| 3 | — | 84 | 2 |
| 20 | — | 78 | 32 |
| 22 | — | — | 83 |
| 23 | 92 | 46 | — |
| 29 | — | 72 | 14 |
| 33 | — | 94 | 45 |
| 45 | 77 | 11 | — |
| 46 | — | 73 | 7 |
| 47 | 80 | 50 | 2 |
| 52 | 94 | 89 | 38 |
| 54 | — | 88 | 12 |
| 75 | 93 | 69 | 15 |
| 79 | 92 | 87 | 46 |
| 81 | 76 | 63 | 8 |
| 90 | 85 | 79 | 9 |

Inhibition of Binding of $^3H$-$LTB_4$ to Peripheral Human Neutrophils

The effectiveness of compounds to inhibit the binding of leukotriene $B_4$ to a specific receptor on the membrane of human neutrophils was measured by using an adaptation of a radio-ligand binding assay developed by Goldman and Goetzl, J. Immunol., 129, 1600 (1982). Other investigators have developed similar assays (see, e.g., Kreisle, et al., J. Exp. Med., 157, 628 (1983) and Lin, et al., Prostaglandins, 28, 837 (1984)).

Cells used in the assay were isolated by standard techniques of centrifugation on Ficoll-Hypaque, dextran 70 sedimentation and hypotonic lysis. The following procedure was used. Freshly-prepared buffy coat layers from two individuals were obtained from a local blood donor center. The cells were mixed and diluted to 484 ml with phosphate buffered saline containing heparin (10 units/ml) and heat-inactivated calf serum (5%). This was divided into 20 ml aliquots and the aliquots layered on top of Ficoll-Paque (12 ml). The material was then centrifuged at 500 g for 40 minutes at room temperature. The resulting upper layer of platelets and mononuclear cells was discarded. The lower layer containing erythrocytes and neutrophils was retained. Buffer was added (1 ml per 4 ml of lower layer) and the suspension mixed. For each milliliter of this mixture, 0.33 ml of 6% Macrodex was added. After stirring, the cells were allowed to sediment for 1 hour at 37° C. The resulting erythrocyte pellet was discarded and the neutrophil enriched supernatant fluid centrifuged at 500 g for 10 minutes at 4° C. Erythrocytes still present in this cell pellet were lysed by incubating the cells with 5–8 ml ice-cold distilled water for 30–45 seconds. Subsequently, the volume was made up to 50 ml by addition of ice-cold buffer and the cells resuspended. The suspension was then centrifuged at 300 g for 10 minutes at 4° C. The cells were finally resuspended at a cell density of $2\times 10^7$ cells/ml in the assay buffer. This buffer consisted of Hanks' balanced salt solution and 0.1% ovalbumin (pH 7.3). This isolation procedure resulted in cell preparations of $\geq 90\%$ neutrophils and $\geq 90\%$ viability.

The radio-ligand binding assay was conducted by incubating neutrophils ($1\times 10^7$ cells) with 0.1–0.2 nM $^3H$-$LTB_4$ (sp. act. 150–220 Curies/mmol) and test compound ($1\times 10^{-5}M$ and $1\times 10^{-6}M$) for 10 minutes at 4° C. The amount of bound $^3H$-$LTB_4$ was then measured and compared with the amount bound in the absence of test compound. The assay was carried out in microcentrifuge tubes by adding first 10 μl test compound dissolved in DMSO, followed by adding 20 μl $^3H$-$LTB_4$ diluted in assay buffer, and finally adding 500 μl of the cell suspension. At the end of the 10 minutes incubation, 300 μl of a mixture of dibutyl and dinonyl phthalate (7:2) were added and the tubes centrifuged for 2 minutes in a microcentrifuge. The radioactivity bound to the cell pellet was measured by scintillation spectroscopy.

Appropriate corrections for nonspecific bonding of $^3$H-LTB$_4$ were made. The results are reported in Table III.

TABLE III

| | LTB$_4$ Binding Inhibition | | |
|---|---|---|---|
| | Drug Concentration* | | |
| Example No. | $10^{-5}$M | $10^{-6}$M | $10^{-7}$M |
| 2 | −11 | 14 | — |
| 3 | 76 | 26 | — |
| 4 | −5 | −1 | — |
| 12 | 3 | −1 | — |
| 15 | −13 | 1 | — |
| 17 | 81 | 20 | — |
| 20 | 71 | 35 | — |
| 21 | 74 | 23 | — |
| 22 | 95 | 62 | 17 |
| 23 | 87 | 52 | 4 |
| 24 | 93 | 28 | — |
| 26 | 63 | 10 | — |
| 27 | 80 | 18 | — |
| 28 | 96 | 55 | — |
| 29 | 98 | 71 | 11 |
| 32 | 19 | −6 | — |
| 33 | 100 | 79 | 17 |
| 35 | 53 | 2 | — |
| 40 | −14 | −10 | — |
| 44 | 41 | 11 | — |
| 45 | 78 | 19 | — |
| 46 | 91 | 55 | 13 |
| 47 | 59 | 2 | — |
| 48 | 10 | −10 | — |
| 50 | 88 | 41 | — |
| 52 | 92 | 61 | 17 |
| 54 | 71 | 37 | −3 |
| 56 | 88 | 41 | — |
| 75 | 97 | 82 | 36 |
| 76 | 96 | 91 | 36 |
| 77 | 22 | 8 | — |
| 78 | 18 | 4 | — |
| 79 | 100 | 97 | 92 |
| 80 | 105 | 98 | 68 |
| 81 | 106 | 91 | 42 |
| 82 | 104 | 81 | 22 |
| 83 | 103 | 79 | 18 |
| 84 | 99 | 91 | 49 |
| 85 | 101 | 97 | 86 |
| 86 | 95 | 88 | 46 |
| 87 | 100 | 91 | 34 |
| 90 | 98 | 96 | 90 |
| 91 | 98 | 88 | 60 |
| 101 | | 88 | 46 |
| 102 | 98 | 72 | 18 |

*percent inhibition

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages of from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

The following formulation examples may employ as active compounds any of the compounds of this invention. The examples are illustrative only and are not intended to limit the scope of the invention in any way.

EXAMPLE 106

Hard gelatin capsules are prepared using the following ingredients:

| | Quantity (mg/capsule) |
|---|---|
| [4-(Decyloxy)-3-(1H-tetrazol-5-ylmethyl)phenyl][3-(1H-tetrazol-5-yl)phenyl]methanone, disodium salt | 250 |
| Starch | 200 |
| Magnesium stearate | 10 |

The above ingredients are mixed and filled into hard gelatin capsules in 460 mg quantities.

EXAMPLE 107

A tablet is prepared using the ingredients below:

| | Quantity (mg/tablet) |
|---|---|
| 5-(3-Carboxybenzoyl)-2-{[6-(4-methoxyphenyl)-5-hexenyl]oxy}-benzenepropanoic acid, potassium | 250 |

| | Quantity (mg/tablet) |
|---|---|
| salt | |
| Cellulose, microcrystalline | 400 |
| Silicon dioxide, fumed | 10 |
| Magnesium stearate | 5 |

The components are blended and compressed to form tablets each weighing 665 mg.

EXAMPLE 108

An aerosol solution is prepared containing the following components:

| | Weight % |
|---|---|
| 5-(3-Carboxybenzoyl)-2-{[6-(4-methoxyphenyl)hexyl]oxy}benzenepropanoic acid, dipotassium salt | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled at −30° C. and transferred to a filling device. The required amount is then fed to a container and further filled with the pre-mixed propellants 12 and 114 by means of the cold-filled method or pressure-filled method. The valve units are then fitted to the container.

EXAMPLE 109

Tablets each containing 60 mg of active ingredient are made up as follows:

| | |
|---|---|
| 5-(3-Carboxybenzoyl)-2-{[6-(4-methylsulfinylphenyl)-5-hexenyl]oxy}-benzenepropanoic acid | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 110

Capsules each containing 80 mg of medicament are made as follows:

| | |
|---|---|
| 5-(3-Carboxybenzoyl)-2-{[6-(4-methylsulfonylphenyl)-5-hexenyl]oxy}benzenepropanoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 111

Suppositories each containing 225 mg of active ingredient are made as follows:

| | |
|---|---|
| 5-(3-Carboxyphenoxy)-2-(decyloxy)-benzenepropanoic acid | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

EXAMPLE 112

Suspensions each containing 50 mg of medicament per 5 ml dose are made as follows:

| | |
|---|---|
| 5-[(3-Carboxyphenyl)(hydroxyimino)methyl]-2-(decyloxy)benzenepropanoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 ml |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

I claim:
1. A compound of the formula

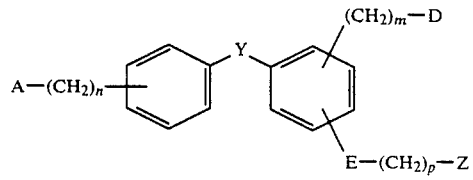

or a pharmaceutically acceptable base addition salt thereof, wherein A and D are each independently —COOH, —COO($C_1$—$C_3$ alkyl), —CN, or 5—tetrazolyl;

n is 0 or 1;
Y is —CO—[, —C(=NOH)—, —CHOH—, —CH$_2$—or —C(=CH$_2$)—];
m is 0–3;

E is —O—pr —CH$_2$—;

p is 0—16; and

Z is —H or —G—Q, where

G is a bond, —O—, —S(O)$_t$—, —NH—, —CH=CH—, or —C≡C—,

Q is phenyl or phenyl substituted with one or two substituents selected from the group consisting of halo, C$_1$-C$_3$ alkyl, C$_1$-C$_3$ alkoxy, acetyl, nitro, amino, trifluoromethyl, hydroxy, and —S(O)$_t$—(C$_1$-C$_3$ alkyl), and each t is independently 0-2, provided that at least one of A and D must be either —CN or —COO(C$_1$-C$_3$ alkyl); and further provided that when m is 0 or 1, p must be 4–16.

2. A compound of claim 1 of the formula

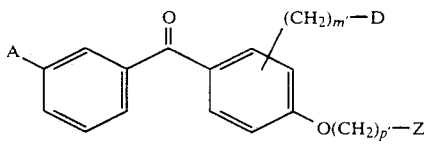

or a pharmaceutically acceptable base addition salt thereof wherein

A and D are independently —COOH or —COO(C$_1$-C$_3$ alkyl);

m' is 2; and p' is 0–12.

3. A compound of claim 2 which is 5-[3-(ethoxycarbonyl) benzoyl]-2-{[6-(4-methoxyphenyl)-5-hexenyl]oxy}-benzenepropanoic acid, ethyl ester.

4. The compound of claim 2 which is 5-[3-(ethoxycarbonyl) benzoly]-2-benzene propanoic acid, ethyl ester.

* * * * *

UNITED STATES PATENT AND TRADEMARK OFFICE
CERTIFICATE OF CORRECTION

PATENT NO. : 4,992,576

DATED : February 12, 1991

INVENTOR(S) : D. Mark Gapinski

It is certified that error appears in the above-identified patent and that said Letters Patent is hereby corrected as shown below:

Column 34, lines 66-67 delete "[, -C(=NOH)-, -CHOH-, -CH$_2$- or -C(-CH$_2$)-]"

Signed and Sealed this

Twenty-first Day of July, 1992

Attest:

DOUGLAS B. COMER

*Attesting Officer*     *Acting Commissioner of Patents and Trademarks*